(12) United States Patent
Serteyn et al.

(10) Patent No.: US 10,633,633 B2
(45) Date of Patent: Apr. 28, 2020

(54) MAMMALIAN MUSCLE-DERIVED STEM CELLS

(71) Applicant: Université de Liège, Liège (BE)

(72) Inventors: Didier Serteyn, Liège (BE); Justine Ceusters, Liège (BE)

(73) Assignee: Universitè De Liège, Liège (BE)

( * ) Notice: Subject to any disclaimer, the term of this patent is extended or adjusted under 35 U.S.C. 154(b) by 799 days.

(21) Appl. No.: 14/911,781

(22) PCT Filed: Dec. 11, 2014

(86) PCT No.: PCT/EP2014/077415
§ 371 (c)(1),
(2) Date: Feb. 12, 2016

(87) PCT Pub. No.: WO2015/091210
PCT Pub. Date: Jun. 25, 2015

(65) Prior Publication Data
US 2016/0186142 A1 Jun. 30, 2016

(30) Foreign Application Priority Data
Dec. 19, 2013 (EP) .................................. 13198477

(51) Int. Cl.
*C12N 5/0775* (2010.01)
*A61K 35/28* (2015.01)

(52) U.S. Cl.
CPC ............ *C12N 5/0668* (2013.01); *A61K 35/28* (2013.01); *C12N 2506/1323* (2013.01); *C12N 2509/00* (2013.01)

(58) Field of Classification Search
None
See application file for complete search history.

(56) References Cited

U.S. PATENT DOCUMENTS

2006/0130852 A1* 6/2006 Smith .................... A61K 35/28
128/898

FOREIGN PATENT DOCUMENTS

WO    WO 2015/091210 A1    6/2015

OTHER PUBLICATIONS

Dominici, M; et al; "Minimal criteria for defining multipotent mesenchymal stromal cells. The International Society for Cellular Therapy position statement" Cytotherapy, 8, 315-317, 2006 (Year: 2006).*
Ceusters J. et al., Assessment of reactive oxygen species production in cultured equine skeletal myoblasts in response to conditions of anoxia followed by reoxygenation with or without exposure to peroxidases, Am. J. Vet. Res., vol. 73, Mar. 1, 2012, pp. 426-434.
Joon Yung et al., Clonal Isolation of Muscle-derived Cells Capable of Enhancing Muscle Regeneration and Bone Healting, the Journal of Cell Biology, Sep. 4, 2000, pp. 9521-9525.
Richardson et al., Stem cells in veterinary medicinse—attempts at regenerating equine tendon after injury, Trends in Biotechnology, Elsevier Publications, Cambridge, GB, vol. 25, No. 9, Aug. 23, 2007, pp. 409-416.
Maritza Mayorga et al., Pre-transplantation Specification of Stem Cells to Cardiac Lineage for Regeneration of Cardiac Tissue, Stem Cell Review and Reports, vol. 5, No. 1, Jan. 30, 2009, pp. 51-60.
Ozgur Sunay et al., Autologous rabbit adipose tissue-derived mesenchymal stromal cells for the treatment of bone injuries with distratction osteogenesis, Cytotherapy, vol. 15, No. 6, Jun. 1, 2013, pp. 690-702.
E. Iacono et al., Isolation, characterization and differentiation of mesenchymal stem cells from anmiotic fluid, umbilical cord blood and Wharton's jelly in the horse, Reproduction, vol. 143, No. 4, Jan. 24, 2012, pp. 455-468.
Catherine L. Radtke et al., Characterization and osteogenic potential of equine muscle tissue-and periosteal tissue-derived mesenchymal stem cells in comparison with bone marrow-and adipose tissue-derived mesenchymal stem cells, American Journal of Veterinary Research, American Veterinary Medicine Association, US, vol. 74, No. 5, May 1, 2013, pp. 790-800.
Xiaxia Che et al., Rapid isolation of muscle-derived stem cells by discontinuous Percoll density gradient centrifugation, In Vitro Cellular & Developmental Diology—Animal, Springer-Verlag, New York, vol. 47, No. 7, Jun. 21, 2011, pp. 454-458.
Wesley M. Jackson et al., Potential therapeutic applications of muscle-derived mesenchymal stem and progenitor cells, Expert Opinion on Biological Therapy, Ashley, London, GB, vol. 10, No. 4, Apr. 1, 2010, pp. 505-517.
Dominici M. et al., Minimal criteria for defining multipotent mesenchymal stromal cells, The International Society for Cellular Therapy position statement, Cytotherapy, Isis Medical Media, Oxford, GB, vol. 8, No. 4, Aug. 1, 2006, pp. 315-317.
Wesley M. Jackson et al., Differentiation and regeneration potential of mesenchymal progenitor cells derived from traumatized muscle tissue, Journal of Cellular and Molecular Medicine, vol. 15, No. 11, Oct. 24, 2011, pp. 2377-2388.
Hairong Peng et al., Muscle-derived stem cells for musculoskeletal tissue regeneration and repair, Translplant Immunology, vol. 12, No. 3-4, Apr. 1, 2004, pp. 311-319.
Daniela Franco Bueno et al., New source of muscle-derived stem cells with potential for alveolar bone reconstruction in cleft lip and/or palate patients, Tissue engineering, Part A, Feb. 1, 2009, pp. 427-435.
Angela Schoolmeesters et al., Functional Profiling Reveals Critical Role for miRNA in Differentiation of Human Mesenchymal Stem Cells, PLOS One, vol. 4, No. 5, May 19, 2009, p. e5605.
Uma Lakshmipathy et al., Concise Review: MicroRNA Expression in Multipotent Mesechymal Stromal Cells, Stem Cells, vol. 26, No. 2, Feb. 1, 2008, pp. 356-363.

(Continued)

*Primary Examiner* — David W Berke-Schlessel
(74) *Attorney, Agent, or Firm* — Harness, Dickey & Pierce, P.L.C.

(57) ABSTRACT

The present invention provides a new method of obtaining muscle-derived mesenchymal stem cells from microbiopsies of mammalian origin. The invention provides for a minimally invasive methodology yielding high amounts of MSCs that can differentiate into different cell lineages.

10 Claims, 6 Drawing Sheets

(56) References Cited

OTHER PUBLICATIONS

Ling Guo et al., The role of micoRNAs in self-renewal and differentiation of mesenchymal stem cells, Experimental Hematology, Elsevier Inc., US, vol. 39, No. 6, Jan. 25, 2011, pp. 608-616.
Gutierrez-Nibeyro, S. D. Commercial cell-based therapies for musculoskeletal injuries in horses. Veterinary Clinics of North America: Equine Practice, 2011, 27, 363-371.
Meloan, S. N., Puchtler, H., Valentine, L. S. Alkaline and acid alizarin red S stains for alkali-soluble and alkali-insoluble calcium deposits. Archives of Pathology, 1972,93(3),190-197.
Pittenger, M. F., Mackay, A. M., Beck, S. C., Jaiswal, R. K., Douglas, R., Mosca, J. D., Moorman, M. A., Simonetti, D. W., Craig, S., Marshak, D. R. Multilineage potential of adult human mesenchymal stem cells (MSCs). Science, 1999, 284 (5411), 143-147.
Schnabel L. V., Fortier L. A., Wayne McIlwraith C., Nobert K. M. Therapeutic use of stem cells in horses: Which type, how, and when? The Veterinary Journal, 2013, 197(3), 570-577.
Usas, A., Madulaitis, J., Madulaitis, R., Jakuboniene, N., Milasius, A., Huard, J. Skeletal muscle-derived stem cells: implications for cell-mediated therapies. Medicina (Kaunas), 2011, 47(9), 469-479.
Votion D. M., Fraipont A., Goachet A. G., Robert C., Van Erck E., Amory H., Ceusters J., De La Rebiere De Pouyade G., Franck T., Mouithys-Mickalad A., Niesten A., Serteyn D. Alterations in mitochondrial respiratory function in response to endurance training and endurance racing. Equine Veterinary Journal, 2010, 42(suppl 38), 268-274.
Adams, M.K., Goodrich, L.R., Rao, S., Olea-Popelka, F., Phillips, N., Kisiday,, J.D., McIlwraith, C.W. Equine bone marrow-derived mesenchymal stromal cells (BMDMSCs) from the ilium and sternum: Are there differences? Equine Veterinary Journal, 2012, 45, 372-375.

* cited by examiner

MAMMALIAN MUSCLE-DERIVED STEM CELLS

CROSS-REFERENCE TO RELATED APPLICATIONS

This application is a U.S. National Stage of International Application No. PCT/EP2014/077415, filed on Dec. 11, 2014, which claims the benefit of, and priority to, European Patent Application No. 13198477.5, filed on Dec. 19, 2013. The entire disclosures of each of the above applications are incorporated herein by reference.

FIELD OF THE INVENTION

The invention relates to the production of mammalian stem cells derived from muscular tissue and uses of such stem cells in treating injured tissue. More particularly, the invention provides the production of mesenchymal stem cells (MSCs) derived from mammalian muscular tissue and the veterinary use of such stem cells in treating injured tissue.

BACKGROUND OF THE INVENTION

The use of stem cells in veterinary medicine such as equine medicine opens the way to a wide range of therapeutic opportunities by promoting an optimal regeneration of the injured tissue. Indeed, tendinitis and osteoarthritis are very frequent pathologies in equine medicine and unfortunately have a poor prognosis. In fact, musculoskeletal injuries are the most common source of injuries for competing horses. Although it is well known that (almost) adult tissues have some tissue-specific progenitor cells, these are often not sufficient for an efficient repair. Thus, effective regenerative medicine requires an exogenous input of cells in greater numbers than those that are present normally within the tissue. These cells should both be able to repair the lesion as well as to coordinate the healing process.

In current equine veterinary practice, the most commonly used stem cells are adult bone marrow-derived and adipose tissue-derived mesenchymal stem cells (MSCs), as well as Wharton's jelly MSCs (Schnabel et al., 2013, Iacono et al., 2012). Bone marrow aspirate is typically harvested from the sternum (marrow spaces 3-5) or ilium (Adams et al., 2012) and adipose tissue is generally harvested from the tail head region (Gutierrez-Nibeyro, 2011). Wharton's jelly is isolated from umblical cord (Iacono et al., 2012). These sampling methods are quite invasive, often not appreciated by owners of competing horses and can provoke some infections.

A second shortcoming for veterinary research is the lack in commercially available specific antibodies. For this, human antibodies need to be used, and their cross reactivity in animals such as horses needs to tested. As an example, only 4% of human antibodies react with equivalent equine proteins. Valid immunophenotyping further necessitates proper use of control isotypes to exclude non-specific antibody reactions and positive control cells to confirm cross reactivity in e.g. horses. There are hence no standard specifications or markers to ensure the quality of the animal or equine stem cells commercially available. Nevertheless, some research groups have tried to effectively characterize mesenchymal stem cells (MSCs) from various animal origins such as: bone marrow, adipose tissue, umbilical cord, umbilical cord blood, Wharton's jelly, peripheral blood and very recently periosteal tissue and muscle (Radtke et al., 2013). Radtke and co-workers in this respect reported on a process for the generation of equine muscle-derived mesenchymal stem cells (MSCs), wherein large muscular biopsies (6 g weight) are collected from horse cadavers. This method is hence highly invasive and not useful for living and competing horses. Secondly, the stem cells obtained are isolated from the biopsies by means of enzyme digestion techniques, which limit the possibilities. Third, the cells obtained by the process of Radtke and co-workers are positive for CD90 and CD44, but negative for CD45, CD34, CD146 and CD105. This negativity for CD105 was reported as being common in equine mesenchymal stem cells (MSCs) by Radtke et al., 2013.

From the above, it is clear that new methods are needed for producing mesenchymal stem cells (MSCs) from mammalians such as horses that involve a minimal invasive effort.

SUMMARY OF THE INVENTION

In summary, stem cells used in regenerative medicine should be present in high quantity, able to be collected and harvested by a minimally invasive procedure, capable of differentiating along multiple cell lineage pathways in a reproducible manner, safely and effectively transplanted either autologously, allogeneicly or xenogenously. Actually, these criteria are not met in current veterinary regenerative medicine.

The present invention therefore provides a new process for the generation of mammalian-derived pluripotent mesenchymal stem cells (MSCs) from a micro-biopsy. A non-invasive muscular micro-biopsy (10-20 mg) is collected on a living animal, for example from muscular tissue from a horse, cultivated and used as explant to initiate the culture. Cells that came out of the explant were centrifuged on a (discontinuous) density gradient to select the part of the cultured cell population with the greatest percentages of pluripotent cells. Immunophenotyping and trilineage differentiation unexpectedly indicated that the cellular populations selected by density gradient centrifugation were found to be mesenchymal stem cells (MSCs), able to differentiate into adipocytes, osteocytes and chondrocytes when cultured in the adequate differentiation medium.

The mesenchymal stem cells (MSCs) of the present invention are positive for CD44, CD90 and CD105 and negative for CD45, MHCII and CD29. This is in contrast with the stem cells obtained by Radtke et al., 2013, which were reported to be CD105 negative. Taking into account the ISCT recommendations for stem cells (Dominici et al., 2006), the MSC populations obtained herein can effectively be classified as pluripotent stem cells since they are highly positive for CD90, CD105 and CD44, negative for CD45, MHCII and unexpectedly for CD29.

The MSCs of the present invention are furthermore positive for miR-128, miR-133B, and miR-802, slightly positive for miR-218 and negative for miR-656. This is in contrast with other MSCs in the art, such as Wharton's jelly MSCs or bone marrow MSCs. Wharton's jelly MSCs are negative for miR-128, miR-133B, miR-218 and miR-802 and positive for miR-656. Bone marrow MSCs are positive for miR-218 and miR-802 and negative for miR-128, miR-133B and miR-656 (cf. Example section). Hence distinct differences exist in the properties of the MSCs of the present invention and MSCs disclosed in the art.

Moreover these cells support a plurality of freeze-thawing cycles without loosing their pluripotency.

The present invention hence offers a more effective and promising alternative to the methods already described in the literature and, for the first time, provides the possibility of being carried out on living animals such as horses due to its minimally invasive character.

In addition, cell culture is initiated with a more simple method than the enzyme digestion technique previously used (Radtke et al., 2013). For this, the muscular microbiopsies are used as explants and progenitor cells appear spontaneously in due time. By doing so, the number of manipulations is reduced, avoiding potential sources of contamination. No external growth factors need to be added, since the growth factors that are naturally secreted by the muscle microbiopsy (the explant) are sufficient.

Muscle-derived cells are a mixture of subpopulations form different lineages and different developmental stages. On the basis of their density, related to their expression of specific molecular markers, and thanks to a (discontinuous) density gradient, the method of the invention is able to select three substantially pure subpopulations of pluripotent mesenchymal stem cells out of the muscular explants.

All three subpopulations comprise >90% of cells that are CD44 positive. For CD90, the rate of expression is 36% for 25-35% fraction, 48% for <15% fraction and 73% for 15-25% fraction. For CD105, the rate of expression varies between 85 and 95% in the three populations. The three populations also show different CFU-F and proliferative properties (cf. Examples section).

In addition, it was shown that said mesenchymal stem cells (MSCs) can form fibroblasts-like colonies in culture. In addition, unlike what is normally observed with other mesenchymal stem cell sources, said cells can also differentiate into adipocytes, chondrocytes and osteocytes and support a plurality of freeze-thawing cycles without lost of their pluripotency.

In an attempt to provide a less-invasive process for the generation of animal muscle-derived mesenchymal stem cells (MSCs), the inventors found that combining muscular microbiopsy, culturing of the explant and further enriching cells that emerged from the explant by (discontinuous) density gradient centrifugation unexpectedly generates MSCs cells. It was totally unexpected that newly generated cells coming from the explant spontaneously during culturing and further enriched by gradient centrifugation were mesenchymal stem cells (MSCs).

The process of the invention allows the generation of a large quantity of mesenchymal stem cells (MSCs) from a very small biopsy (microbiopsy), without an enzyme digestion step. Such an anzyme digesion step would in any case be impossible to apply to a microbiopsy as confirmed in Freshney, R. I. et al., 2005 (Culture of animal cells: A manual of basic technique. 5th Edition, Wiley, New York) disclosing that the required amount of tissue for the cultivation after an enzymatic digestion is about 1-5 g.

The MSCs obtained by the method according to the present invention express CD105, which is a component of the TGF beta1 complex, having different important biological functions such as angiogenesis and growth induction at the joint/articular level. For a comprehensive review of TGF beta signaling in cartilage, please see Finnson K W et al., 2012 (Front Biosci (Schol Ed). January 1; 4:251-68). TGF beta1 stimulates chondrocyte division as well as cartilage matrix synthesis. It is moreover found in platelets derivatives, like platelet-rich plasma, i.e. blood plasma that has been enriched with platelets (PRP) (Lubkowska A et al., 2012, J Biol Regul Homeost Agents. April-June; 26(2 Suppl 1):3S-22S). As a concentrated source of autologous platelets, PRP contains (and releases through degranulation) several different growth factors and other cytokines that stimulate healing of bone and soft tissue. Furthermore TGF beta1 decreases the release of PGE2 by osteoarthritic synovial fibroblasts and hence decreases PGE2 stimulated matrix degradation in osteoarthritis (Fernandes J. C. et al., 2002, Biorheology, 39, 237-46). The CD105 expression on the MSCs of the invention hence seems to give excellent tissue regeneration characteristics to the obtained stem cells.

The invention hence provides the following aspects:

Aspect 1. A method for preparing mammalian mesenchymal stem cells (MSCs) comprising the steps of:
  a) collecting a microbiopsy from said mammal,
  b) after collection, placing said microbiopsy in suitable culture medium,
  c) collecting cells emerging from said microbiopsy during culturing,
  d) growing the cells obtained in step c) to near confluency,
  e) dissociating the cells from step d),
  f) Separating mesenchymal stem cells (MSCs) from the other cells by density gradient fractionation, thereby obtaining mesenchymal stem cells (MSCs). Said cells can optionally be further purified by one or more sub-culturing or passaging steps.

Aspect 2. The method according to aspect 1, wherein said microbiopsy is obtained from skeletal muscle tissue, such as from muscles from the neck, shoulder, chest, back, tail, limbs, hindlimb, forelimb, hindquarters, hindleg etc. preferably from triceps brachii muscle tissue, more preferably taken from the long head of the triceps brachii.

Aspect 3. The method according to aspect 2, wherein said microbiopsy is collected at a depth of about 5 cm in the long head of the long head of the triceps brachii.

Aspect 4. The method according to any one of aspects 1 to 3, wherein said microbiopsy contains about 15 to about 20 mg of tissue.

Aspect 5. The method according to any one of aspects 1 to 4, wherein said culture medium comprises DMEM/F12 with about 20% fetal bovine serum, about 5 ml penicillin (1000 U/ml)-streptomycin (10000 μg/ml), about 2.5 ml amphotericin B (250 μg/ml) and about 5 ml HEPES.

Aspect 6. The method according to any one of aspects 1 to 5, wherein in step d) the cells from the density fraction below 35% is obtained.

Aspect 7. The method according to aspect 6, wherein in step d) the cells from density fractions <15%, 15-25%, and/or 25-35% are obtained.

Aspect 8. The method according to any one of aspects 1 to 7, wherein said mammal is selected from the group comprising: domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes.

Aspect 9. A mesenchymal stem cell population obtained by the method according to any one of aspects 1 to 8.

Aspect 10. A mesenchymal stem cell population, or the mesenchymal stem cell population according to aspect 9, characterized in that said cells express CD105, preferably wherein said cells express CD105 in combination with CD44 and/or CD90.

Aspect 11. The mesenchymal stem cell population according to aspect 9 or 10, characterized in that said cells do not express the following markers: CD45, MHC II and CD29.

Aspect 12. The mesenchymal stem cell population according to any one of aspects 9 to 11, characterized in that said cells express at least one microRNA selected from the group comprising: miR-128 and miR-133B.

Aspect 13. The mesenchymal stem cell population according to any one of aspects 9 to 12, characterized in that said cells do not express the following microRNA: miR-656.

Aspect 14. A pharmaceutical or veterinary composition comprising the mesenchymal stem cells obtained according to the method of any one of aspects 1 to 8, or comprising a mesenchymal stem cell population according to any one of aspects 9 to 13.

Aspect 15. The mesenchymal stem cell population according to any one of aspects 9 to 13, or the pharmaceutical or veterinary composition of aspect 14, for use as a medicament or as a pharmaceutical or veterinary agent.

Aspect 16. The mesenchymal stem cell population according to any one of aspects 9 to 13, or the pharmaceutical or veterinary composition of aspect 14, for use in treating one or more of the following disorders: desmitis, osteochondrosis, arthritis, osteoporosis, tendonitis, laminitis, inflammation of the tendons and ligaments, fracture, and failure to heal in a mammalian subject.

Aspect 17. The mesenchymal stem cell population for use according to aspects 15 or 16, wherein autologous, allogeneic, or xenogenic mesenchymal stem cells (MSCs) are used.

Aspect 18. The method according to any one of aspects 1 to 8, additionally comprising the step of differentiating the cells into adipocytes, osteocytes, chondrocytes, myogenic cells, hematopoetic cells, endothelial cells, neural cells, cardiac cells, or hepatocytes by culturing the MSCs in an adequate adipogenic, osteogenic, chondrogenic, myogenic, hematopoetic, endothelial, neuronal, cardial, or hepatocytic differentiation medium respectively. Preferably, the method according to any one of aspects 1 to 8 comprises the step of differentiating the cells into adipocytes, osteocytes or chondrocytes, by culturing the MSCs in an adequate adipogenic, osteogenic, or chondrogenic differentiation medium respectively.

Aspect 19. Differentiated adipocytes, osteocytes or chondrocytes, myogenic cells, hematopoetic cells, endothelial cells, neural cells, cardiac cells, or hepatocytes, obtained by the method according to aspect 18.

Aspect 20. A pharmaceutical or veterinary composition comprising the differentiated adipocytes, osteocytes or chondrocytes according to aspect 19.

Aspect 21. The differentiated adipocytes, osteocytes or chondrocytes according to aspect 19, or the pharmaceutical or veterinary composition of aspect 20, for use in treating one or more of the following disorders: desmitis, osteochondrosis, arthritis, osteoporosis, tendonitis, laminitis, inflammation of the tendons and ligaments, fracture, and failure to heal in a mammalian subject.

Aspect 22. A method of treating one or more of the following disorders: desmitis, osteochondrosis, arthritis, osteoporosis, tendonitis, laminitis, inflammation of the tendons and ligaments, fracture, and failure to heal in a mammalian subject comprising the step of administering to said subject a therapeutically effective amount of MSCs obtained through the method of any of aspects 1 to 8, or of the veterinary or pharmaceutical composition according to aspect 14, thereby treating said one or more disorder(s) in said mammalian subject.

Aspect 23. A method of treating one or more of the following disorders: desmitis, osteochondrosis, arthritis, osteoporosis, tendonitis, laminitis, inflammation of the tendons and ligaments, fracture, and failure to heal in a mammalian subject comprising the step of administering a therapeutically effective amount of differentiated adipocytes, osteocytes or chondrocytes, myogenic cells, hematopoetic cells, endothelial cells, neural cells, cardiac cells, or hepatocytes obtained through the method of aspect 18, or of the veterinary or pharmaceutical composition according to aspect 20, thereby treating said one or more disorder(s) in said mammalian subject.

Aspect 24. The methods according to aspect 22 or 23, wherein said administered cells are autologous, allogeneic, or xenogenic.

BRIEF DESCRIPTION OF THE FIGURES

The present invention is illustrated by the following figures which are to be considered for illustrative purposes only and in no way limit the invention to the embodiments disclosed therein.

DETAILED DESCRIPTION OF THE INVENTION

Figure 1:
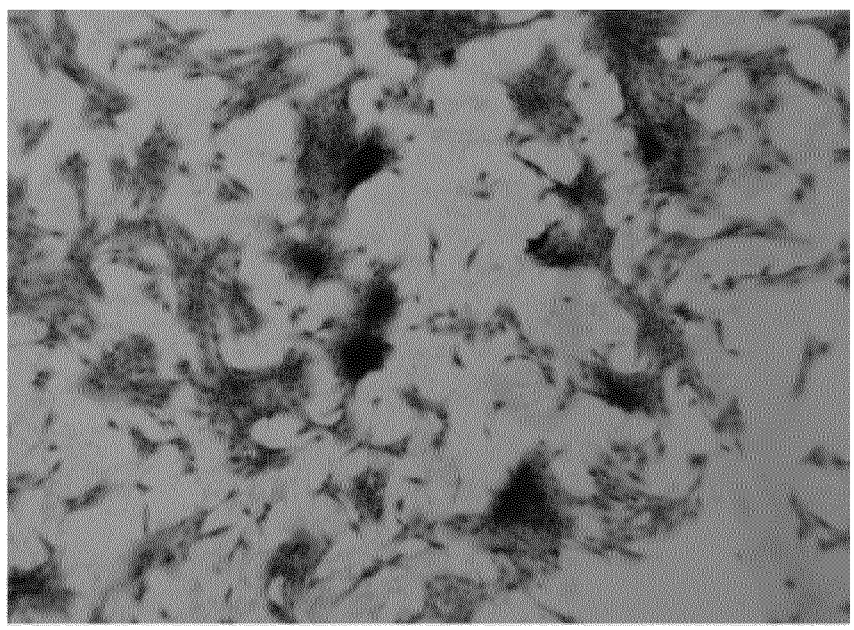
FIG. 1: Representative microscopic photography of morphological aspect of fibroblasts-like colony forming units obtained with cells from each Percoll fraction seeded at low density (500000 cells/flask) and grown for 10 days (May-Grunwald Giemsa staining; A: 100×; B: 400× magnification).
Figure 1:
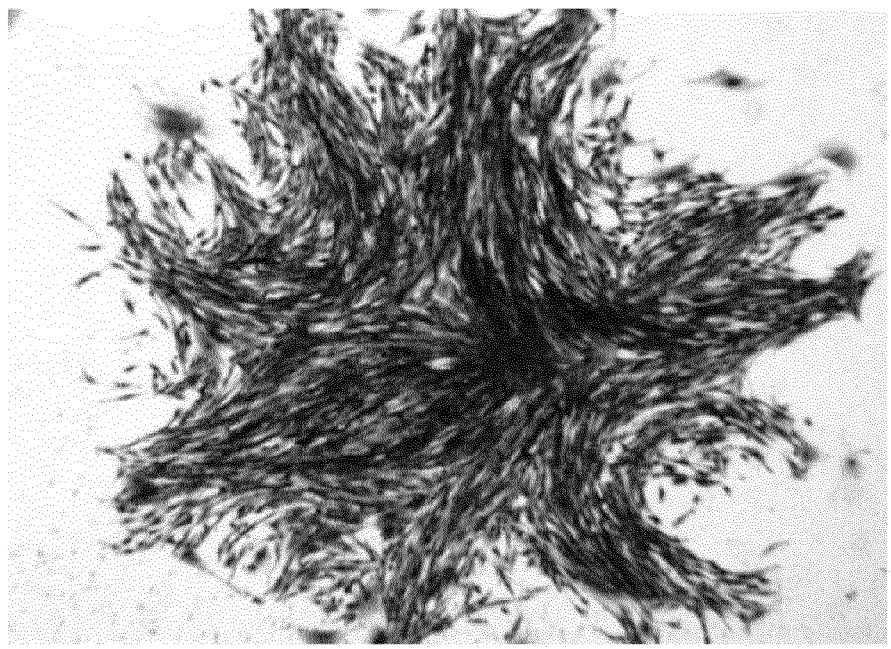

As used herein, the singular forms "a", "an", and "the" include both singular and plural referents unless the context clearly dictates otherwise. By way of example, "a cell" refers to one or more than one cell.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

For general methods relating to the invention, reference is made to well-known textbooks, including, e.g., "Molecular Cloning: A Laboratory Manual, 2nd Ed." (Sambrook et al., 1989), Animal Cell Culture (R. I. Freshney, ed., 1987), the series Methods in Enzymology (Academic Press), Gene Transfer Vectors for Mammalian Cells (J. M. Miller & M. P. Calos, eds., 1987); "Current Protocols in Molecular Biology and Short Protocols in Molecular Biology, 3rd Ed." (F. M. Ausubel et al., eds., 1987 & 1995); Recombinant DNA Methodology II (R. Wu ed., Academic Press 1995), incorporated by reference herein.

For further elaboration of general techniques useful in the practice of this invention, the practitioner can refer to standard textbooks and reviews in cell biology, tissue culture, and embryology. Included are "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cell Differentiation in Vitro" (M. V. Wiles, Meth. Enzymol. 225:900, 1993); "Properties and uses of Embryonic Stem Cells: Prospects for Application to Human Biology and Gene Therapy" (P. D. Rathjen et al., al., 1993). Differentiation of stem cells is reviewed, e.g., in Robertson. 1997. Meth Cell Biol 75: 173; and Pedersen. 1998. Reprod Fertil Dev 10: 31, and Usas et al., 2011, incorporated by reference herein.

General techniques in cell culture and media collection are outlined in Large Scale Mammalian Cell Culture (Hu et al. 1997. Curr Opin Biotechnol 8: 148); Serum-free Media (K. Kitano. 1991. Biotechnology 17: 73); Large Scale Mammalian Cell Culture (Curr Opin Biotechnol 2: 375, 1991), incorporated by reference herein.

The term "stem cell" refers generally to an unspecialised or relatively less specialised and proliferation-competent cell, which is capable of self-renewal, i.e., can proliferate without differentiation, and which or the progeny of which can give rise to at least one relatively more specialised cell type. The term encompasses stem cells capable of substantially unlimited self-renewal, i.e., wherein the progeny of a stem cell or at least part thereof substantially retains the unspecialised or relatively less specialised phenotype, the differentiation potential, and the proliferation capacity of the mother stem cell, as well as stem cells which display limited self-renewal, i.e., wherein the capacity of the progeny or part thereof for further proliferation and/or differentiation is demonstrably reduced compared to the mother cell. By means of example and not limitation, a stem cell may give rise to descendants that can differentiate along one or more lineages to produce increasingly relatively more specialised cells, wherein such descendants and/or increasingly relatively more specialised cells may themselves be stem cells as defined herein, or even to produce terminally differentiated cells, i.e., fully specialised cells, which may be post-mitotic.

The term "mesenchymal stem cell" or "MSC" as used herein refers to a mammalian adult, mesoderm-derived stem cell that is capable of generating cells of mesenchymal lineages, typically cells of two, preferably of three or more mesenchymal lineages, e.g., osteocytic (bone), chondrocytic (cartilage), myocytic (muscle), tendonocytic (tendon), fibroblastic (connective tissue), adipocytic (fat) and stromogenic (marrow stroma) lineage. Commonly, but without limitation, a cell may be considered MSC if it is capable of forming cells of each of the adipocytic, chondrocytic and osteocytic lineages, using standard, art-accepted differentiation conditions and cellular phenotype evaluation methods, e.g., as described in Pittenger et al. 1999 (Science 284: 143-7) or Barberi et al., 2005 (PLoS Med 2: e161), and Usas et al., 2011.

The term MSC also encompasses the progeny of MSC, e.g., progeny obtained by in vitro or ex vivo propagation of MSC obtained from a biological sample of a subject.

The term "isolating" with reference to a particular component denotes separating that component from at least one other component of a composition from which the former component is thereby "isolated". The term "isolated" used in relation to any cell, group of cells or a cell population also implies that such cell, group of cells or cell population does not form part of an animal body.

The ISCT determined precisely the qualities cells must possess to be defined as mesenchymal stem cells (MSCs) as follows: the cells must be plastic-adherent, positive for the markers CD73, CD90 and CD105, negative for the markers CD14 (or CD11 b), CD34, CD45, CD79a (or CD19) and MHC-II, and must exhibit the ability to differentiate into cells of mesodermal origin such as osteoblasts, chondroblasts and adipocytes (Dominici et al., 2006). The use of other MSC markers such as CD29 or CD44 was also reported (Pittenger et al., 1999). The ISCT criteria were extended to the invention herein. The mammalian MSC cells of the present invention hence are defined in that they express or co-express (i.e., are positive for) at least the mesenchymal marker CD105, and preferably also one or more of the following markers: CD44 and CD90. The mammalian MSC cells of the present invention are also defined in that they express or co-express (i.e., are positive for) one or more of the following microRNAs: miR-128, miR-133B, miR-218 or miR-802. The mammalian MSC cells of the present invention are also defined in that they do not express miR-656.

Throughout this specification "co-express" intends to cover the meaning "comprising co-expression of" such that the cells can express other markers or microRNAs in addition to the particular recited markers or microRNAs characterising the cells.

The terms microRNA, miRNA, miR or eca-miR are used herein interchangeably, and refer to 19-25 nucleotides mature non-coding RNAs or precursors thereof, or fragments thereof, derived from endogenous genes of living organisms such as animals. Mature microRNAs are processed from longer hairpin-like precursors termed pre-microRNAs (pre-miRs) having a length of approximately 75 nucleotides.

Where a cell is said to be positive for a particular marker or microRNA, this means that a skilled person will conclude the presence or evidence of a distinct signal, e.g., antibody-detectable or detection by reverse transcription polymerase chain reaction, for that marker or microRNA when carrying out the appropriate measurement, compared to suitable controls. Where the method allows for quantitative assessment of the marker or microRNA, positive cells generate a signal that is significantly different from and higher or stronger than the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

The expression of cell-specific markers can be detected using any suitable immunological technique known in the art, such as immuno-cytochemistry or affinity adsorption, Western blot analysis, FACS, ELISA, etc., or by any suitable biochemical assay of enzyme activity, or by any suitable technique of measuring the quantity of the marker mRNA, e.g., Northern blot, semi-quantitative or quantitative RT-PCR, etc.

The expression of microRNAs may be determined, for example, with an assay for global gene expression (e.g. using a microarray assay for microRNAs expression profiling analysis, a ready-to-use microRNA qPCR plate or RNA sequencing) or by specific detection assays, for example, but not limited to, quantitative PCR, quantitative reverse-transcription (real-time) PCR (qRT-PCR), locked nucleic acid (LNA) real-time PCR, or northern blotting. In particular, the measurement of the expression of a microRNA may be carried out with an oligonucleotide probe specific for the detection of said microRNA. Said oligonucleotide probe may bind directly and specifically to the microRNA, or may specifically reverse transcribe said microRNA. Alternatively, said oligonucleotide probe may bind a cDNA obtained from said microRNA. Said oligonucleotide probe may also amplify a cDNA obtained form said microRNA.

Nucleic and amino acid sequence data for marker proteins listed in this disclosure are generally known and can be obtained from public databases such as, among others, from the NIH "Protein Reviews on the Web" database (http://mpr.nci.nih.gov/prow/), the NIH "Entrez Gene" database (http://www.ncbi.nlm.nih.gov/sites/entrez?db=gene) or the Uniprot/Swissprot database (http://www.expasy.org/). Suitable detection reagents and methods for said markers can be designed either on the basis of such sequence information or, more commonly, are available commercially (e.g., labelled monoclonal antibody reagents).

The term "CD105" encompasses the antigen known as CD105, or its synonyms such as endoglin. CD105 is a membrane glycoprotein located on cell surfaces and is a known mesenchymal stem cell marker. As an example, the partial amino acid sequence of the equine CD105 antigen can be found in the Genbank database under accession number AGW16345.1.

The term "CD90" encompasses the antigen CD90, or its synonyms such as Thy-1 membrane glycoprotein. As an example, the amino acid sequence of the equine CD90 antigen can be found in the Genbank database under accession number ACG61223.1.

The term "CD44" encompasses the antigen generally known as CD44, or its synonyms such as Extracellular matrix receptor III, GP90 lymphocyte homing/adhesion receptor, HUTCH-I, Hermes antigen, Hyaluronate receptor, or Phagocytic glycoprotein 1. As an example, the amino acid sequence of the equine CD44 antigen can be found in the Genbank database under accession number CAA47331.1.

Exemplary commercially available antibody reagents for detection of said MSC markers include inter alia monoclonal antibodies anti-CD105-RPE (ABD Serotec), anti-CD44-APC (BD Pharmigen), and anti-CD90 (VMDR). Alternative antibodies that are specifically binding to CD105, CD44, or CD90 can be identified by the person skilled in the art.

In an embodiment, the MSCs express at least one mesenchymal marker chosen from: CD105, CD90 and CD44. Preferably, the MSCs express at least mesenchymal marker CD105. The invention contemplates MSC cells, which co-express CD105 and CD90, cells which co-express CD90 and CD44, as well as cells which co-express CD105 and CD44. Also covered are cells, in particular MSC cells, which co-express CD105, CD90, and CD44. As shown in the examples, MSC cells of the above marker profile may also co-express other markers.

In another embodiment, the MSCs express at least one microRNA selected from the group comprising: miR-128 and miR-133B. The invention contemplates MSCs which express at least miR-128 or MSCs which express at least miR-133B. Also covered are MSCs which co-express miR-128 and miR-133B. In a further embodiment, the MSCs do not express the following microRNA: miR-656.

MicroRNAs listed in this disclosure are generally known and can be obtained from public databases such as, among others, the miRBase database (http://www.mirbase.org).

The term "miR-128" encompasses the microRNA known as miR-128 or its precursor. As an example, the nucleotide sequence of the equine miR-128 can be found in the miRBase database under accession number MI0012821.

The term "miR-133B" encompasses the microRNA known as miR-133B or its precursor. As an example, the nucleotide sequence of the equine miR-133B can be found in the miRBase database under accession number MI0012844.

The term "miR-656" encompasses the microRNA known as miR-656 or its precursor. As an example, the nucleotide sequence of the equine miR-656 can be found in the miRBase database under accession number MI0012915.

The skilled person is well aware that microRNAs may be referred to by different names, or synonyms.

The MSC cells may further display certain morphological features, such as any one or more of adherence to tissue culture plastic; growth in monolayers; and mononuclear ovoid, stellate or spindle shape with round to oval nuclei having prominent nucleoli.

The term "cell population" generally refers to a grouping of cells. A cell population may consist of or may comprise at least a fraction of cells of a common type, or having characteristics in common. Such characteristics may include, without limitation, morphological characteristics, potential for differentiation (e.g., pluripotent, multipotent, unipotent, etc.; e.g., if multipotent or unipotent, ability to differentiate towards specific cell types), or the presence and/or level of one, two, three or more cell-associated markers, e.g., surface antigens. Such characteristics may thus define a cell population or a fraction thereof. Preferably, such a cell population is mesenchymal stem cell population, more preferably a substantially homogenous population of mesenchymal stem cells.

The term "substantially homogeneous" or "substantially pure" population of mesenchymal stem cells denotes a cell population comprising a fraction of MSCs as defined above, wherein said fraction in said cell population is at least 50%, e.g., at least 55%, preferably at least 60%, e.g., at least 65%, more preferably at least 70%, e.g., at least 75%, even more preferably at least 80%, e.g., at least 85%, most preferably at least 90%, e.g., at least 91%, at least 92%, at least 93%, at least 94%, at least 95%, at least 96%, at least 97%, at least 98%, at least 99%, or even close to or equal to 100%.

The expression "density gradient centrifugation" encompasses all types of cell-separation techniques or products encompassing the density-based separation of cells. Non-limiting examples can be density gradient centrifugation in a gradient of sucrose polymer, or colloidal silica. Non-limiting examples of commercially available gradients are: percoll (colloidal silica coated with polyvinylpyrrolidone or silane), ficoll (high molecular weight sucrose-polymers), Ficoll-Paque (Ficoll plus sodium diatrizoate and edetate calcium disodium), buoyant density solution (BDS, comprising colloidal silica), lymphoprep (sodium diatrizoate and polysaccharide), etc. It is clear that the skilled artisan will be able to select suitable gradients to separate the stem cells obtained with the method according to the present invention. Using the methods of the present invention, the mesenchymal stem cells (MSCs) are typically found in the <15%, 15-25%, or 25-35% Percoll density interfaces, after centrifugation at 1250×g (25° C., 20 min). Mesenchymal stem cells co-expressing the desired marker proteins can then be selected, enriched or isolated from the general population of isolated and optionally expanded cells by methods known per se, such as, for example, using fluorescence activated cell-sorting (FACS), magnetic-activated cell sorting (MACS), affinity-based technologies inter alia affinity chromatography, or the preplate technique and combinations thereof. Exemplary methods are reported in Wu et al., 2010 (cf. Cell Tissue Research, June; 340(3):549-67).

Live cells having a desired expression profile are allowed to bind with reagents (most commonly immunological reagents such as, e.g., monoclonal antibodies) specific for the respective markers, wherein said reagents are in turn modified (e.g., by a fluorophore, or by immobilisation on magnetic particles or another type of stationary phase), such as to facilitate for selection or capture of cells bound by said reagents from cells not so bound. For general guidance on these methods, refer inter alia to Flow Cytometry and Cell Sorting, 2nd ed., by Andreas Radbruch (ed.), Springer 1999 (ISBN 3540656308); In Living Color: Protocols in Flow Cytometry and Cell Sorting, 1st ed., by RA Diamond and S Demaggio (eds.), Springer 2000 (ISBN 3540651497); Flow Cytometry Protocols (Methods in Molecular Biology), 2nd ed., by T S Hawley and R G Hawley (eds.), Humana Press 2004 (ISBN 1588292355); Affinity Separations: A Practical Approach, P Matejtschuk (ed.), Oxford University Press, 1997 (ISBN 0199635501); and Dainiak et al. 2007. Adv Biochem Eng Biotechnol 106: 1-18.

The expression "suitable culture medium" encompasses all cell-culturing media that support the survival and/or growth of the cells mesenchymal stem cells (MSCs) or mesenchymal stem cell populations. Non-limiting examples are: DF20, DMEM-Ham's F12, DMEM, Alpha-MEM etc., typically supplemented with at least antibiotics and fetal bovine serum (FBS), and optionally with antifungal agents and buffers.

As an example only, the following culture medium has been used in the examples: DF20 medium comprising: DMEM/F12 with about 20% fetal bovine serum, about 5 ml penicillin (1000 U/ml)-streptomycin (10000 μg/ml), about 2.5 ml amphotericin B (250 μg/ml) and about 5 ml HEPES.

For differentiation into e.g. adipocytes, osteocytes and chondrocytes, the MSCs or mesenchymal stem cell populations of the invention where cultured in an adequate "differentiation medium". Said differentiation medium can for example be: for adipogenic differentiation: NH AdipoDiff Medium (Miltenyi Biotec); for chondrogenic differentiation: chondrocyte differentiation medium (NH ChondroDiff Medium; Miltenyi Biotec); for osteogenic differentiation: osteogenic medium (NH OsteoDiff Medium; Miltenyi Biotec). The media listed herein are merely shown as exemplary media, but the skilled person will be able to use any other commercial or specifically developed differentiation medium. Other examples of suitable differentiation media for other cells such as myogenic cells, hematopoetic cells, endothelial cells, neural cells, cardiac cells, or hepatocytes can be done by culturing the MSCs in an adequate myogenic, hematopoetic, endothelial, neuronal, cardial, or hepatocytic differentiation medium respectively, examples of which can e.g. be found in Usas et al., 2011.

Appropriate ways of "detaching", "dispersing", "dissociating" or "disassociating" cells are generally known in the art and may be used in the present invention. These involve, e.g., treatment with proteolytic enzymes, chelation of bivalent ions, mechanical disintegration, or combinations of any of the above. Preferably, said cell dissociation may involve enzymatic digestion, favourably using trypsin (e.g., as described above), optionally in combination with chelation of bivalent ions, favourably using EDTA (e.g., as described above), and/or mechanical dissociation of the so-treated cells. The latter may involve, e.g., repeated passing of the cells through a small bore pipette (e.g., a 1000 μl micropipette tip) and/or pipetting out a stream of a suspension containing the cells against a solid surface (e.g., against the wall of the culture vessel). In this way a cell suspension comprising MSCs of the invention can be obtained.

The term "microbiopsy" encompasses all minimally invasive and preferable suture-free subcutaneous collection methods of a tissue sample. The sample size of a microbiopsy is, as the term defines, very small and typically comprises about 15 to about 20 mg of tissue. Any possible technique or device suitable for collecting microbiopsies can be used. Non-limiting examples are microbiopsy needles, conchotomes or spring-loaded micro-biopsy systems known in the art. As an example only, a 14-gauge microbiopsy needle and a microbiopsy pistol can be used.

The source of the microbiopsy used in the method of the present invention for isolating mesenchymal stem cells (MSCs) is preferably skeletal muscle-related tissue from mammals. Examples of skeletal muscle-related tissues are muscles of the neck, shoulder, chest, back, tail, limbs, hindlim, forelimb, hindquarters, hindleg etc. The exemplary used muscle tissue in the examples is the triceps brachii muscle from horse, more preferably, taken from the long head of the triceps brachii, most preferably taken at a depth of about 5 cm in the long head of the long head of the triceps brachii. Harvesting muscle tissue is preferable to e.g. bone marrow or periosteal tissue, because of the quantity but also of the easiness of access of muscular tissue and the low morbidity at this donor site. Embryonic tissue is explicitly excluded as a source of microbiopsy. A study performed by Votion et al., 2010 demonstrated that microbiopsy performed by veterinarians in clinical practice is feasible. Furthermore, the absence of adverse effects permits consideration of this method of sample collection for use on high-performance horses, even during competitions (Votion et al., 2010) and is already used to successfully initiate, by explant method, a primary culture of equine skeletal myoblasts (Ceusters et al., 2012).

The expression "mammal" or "mammalian" refers to all mammals, including, but not limited to, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Preferred mammals are horses, dogs, or cats.

As explained herein, the mesenchymal stem cells obtained from said microbiopsies are cells that spontaneously emerge around the microbiopsy when cultured according to the method as claimed. The term "emerging" encompasses the spontaneous occurrence of cells, i.e. without the need of manipulation of the biopsy, or without the need of adding additional growth, differentiation, or other factors or agents. The culturing step of the microbiopsy, also called explant at this stage, unexpectedly and spontaneously generates mesenchymal stem cells that can be further subcultured, purified and preserved by e.g. cryopreservation as defined herein. Suitable media for said culturing of said microbiopsy are DF20, DMEM-Ham's F12, DMEM, Alpha-MEM etc. Said media are typically containing or are supplemented with at least antibiotics and fetal bovine serum (FBS), and optionally with antifungal agents and buffers.

The present invention provides also methods of treatment by administering the differentiated or non-differentiated MSCs or differentiated or non-differentiated mesenchymal stem cell populations as defined herein particularly to be given to subjects in need thereof, which phrase includes subjects that would benefit from treatment of a given condition, such as myo-arthro-skeletal disorders. Such subjects may include, without limitation, those that have been diagnosed with said condition, those prone to develop said condition and/or those in whom said condition is to be prevented.

The term "subject" encompasses all mammals, including, but not limited to, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Preferred subjects are horses, dogs, or cats.

The terms "treat" or "treatment" encompass both the therapeutic treatment of an already developed disorder, such as the therapy of an already developed myo-arthro-skeletal disorder, as well as prophylactic or preventative measures, wherein the aim is to prevent or lessen the chances of incidence of an undesired affliction, such as to prevent the chances of contraction and progression of a myo-arthro-skeletal disorder such as but not limited to: desmitis, osteochondrosis, arthritis, osteoporosis, tendonitis, inflammation of the tendons and ligaments, fracture, and failure to heal. Beneficial or desired clinical results of such a treatment may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of the veterinary or pharmaceutical composition according to the invention that inhibits or delays in a subject the onset of a disorder as being sought by a researcher or veterinarian. The term "therapeutically effective amount" as used herein, refers to an amount of the veterinary or pharmaceutical composition according to the invention that elicits the biological or medicinal response in a subject that is being sought by a researcher, or veterinarian, which may include inter alia alleviation of the symptoms of the disease or disorder being treated. Methods are known in the art for determining therapeutically and prophylactically effective doses.

The treatment may employ autologous (i.e., cells derived from the subject to be treated), allogeneic (i.e., cells derived from subject(s) other than the subject to be treated, but belonging to the same species) or xenogenic (i.e., cells derived from subject(s) belonging to species other than the subject to be treated) MSCs, differentiated MSCs or their respective cell populations as defined herein.

The veterinary or pharmaceutical compositions will typically comprise the mesenchymal stem cells, differentiated mesenchymal stem cells, or respective (differentiated) mesenchymal stem cell populations of the invention as the active ingredient, and one or more pharmaceutically acceptable carrier/excipient. As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for veterinary or pharmaceutical active substances is well known in the art. Such materials should be non-toxic and should not interfere with the activity of the cells. For veterinary use, the cells could also be formulated in, or administered as, a feed supplement.

The precise nature of the carrier or excipient or other material will depend on the route of administration. For example, the composition may be in the form of a parenterally acceptable aqueous solution. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

Such veterinary or pharmaceutical compositions may contain further components ensuring the viability of the (differentiated) mesenchymal stem cells or cell populations therein. For example, the compositions may comprise a suitable buffer system (e.g., phosphate or carbonate buffer system) to achieve desirable pH, more usually near neutral pH, and may comprise sufficient salt to ensure isoosmotic conditions for the MSCs to prevent osmotic stress. For example, suitable solution for these purposes may be phosphate-buffered saline (PBS), sodium chloride solution, Ringers Injection or Lactated Ringers Injection, as known in the art. Further, the composition may comprise a carrier protein, e.g., albumin, which may increase the viability of the MSCs.

The veterinary or pharmaceutical compositions may comprise further components useful in the repair of bone wounds and defects. For example, such components may include without limitation bone morphogenetic proteins, bone matrix (e.g., bone matrix produced in vitro by cells of the invention or by other methods), hydroxyapatite/tricalcium phosphate particles (HA/TCP), gelatine, poly-lactic acid, poly-lactic glycolic acid, hyaluronic acid, chitosan, poly-L-lysine, and collagen. For example, the osteoblastic cells may be combined with demineralised bone matrix (DBM) or other matrices to make the composite osteogenic (bone forming in it own right) as well as osteo-inductive. Similar methods using autologous bone marrow cells with allogeneic DBM have yielded good results.

The veterinary or pharmaceutical composition can further include or be co-administered with a complementary bioactive factor such as a bone morphogenic protein, such as BMP-2, BMP-7 or BMP-4, or any other growth factor. Other potential accompanying components include inorganic sources of calcium or phosphate suitable for assisting bone regeneration (WO 00/07639). If desired, cell preparation can be administered on a carrier matrix or material to provide improved tissue regeneration. For example, the material can be a granular ceramic, or a biopolymer such as gelatine, collagen, osteonectin, fibrinogen, or osteocalcin. Porous matrices can be synthesized according to standard techniques (e.g., Mikos et al., Biomaterials 14: 323, 1993).

The veterinary or pharmaceutical composition can further include or be co-administered with a complementary disinfecting, aseptic, or microorganism destroying agent such as a bactericidal, antibacterial, antibiotic, or antifungal and/or an anti-inflammatory agent in order to avoid complications due to infection and or inflammation at the site of introduction or administration of the MSCs.

In a further aspect, the invention relates to an arrangement comprising a surgical instrument for administration of the MSC-comprising composition to a subject, such as for example systemically, topically or at a site of a lesion, and further comprising the MSCs or cell populations of the invention, or a veterinary or pharmaceutical composition comprising said MSCs or cell populations, wherein the arrangement is adapted for administration of the veterinary or pharmaceutical composition for example systemically, topically or at the site of bone lesion. For example, a suitable surgical instrument may be capable of injecting a liquid composition comprising MSCs or cell populations of the present invention, such as systemically or at the site of bone lesion.

The MSCs or cell populations can be administered in a manner that permits them to graft or migrate to the intended tissue site and reconstitute or regenerate the functionally deficient area. Administration of the composition will depend on the myo-arthro-skeletal site being repaired. For example, the MSCs or cell populations can be administrated either directly in the lesions (such as for example in tendon or ligament), or in the synovial joints (such as for example the tendinous or articular synovials).

For example, osteogenesis can be facilitated in concordance with a surgical procedure to remodel tissue or insert a split, or a prosthetic device. In other circumstances, invasive surgery will not be required, and the composition can be administered by injection, such as ultra-sound guided injection, or using a guidable endoscope.

In another embodiment, the differentiated or undifferentiated MSCs or mesenchymal stem cell populations of the invention may be transferred to and/or cultured on suitable substrates to provide for implants. The substrate on which the cells can be applied and cultured can be a metal, such as titanium, cobalt/chromium alloy or stainless steel, a bioactive surface such as a calcium phosphate, polymer surfaces such as polyethylene, and the like. Although less preferred, siliceous material such as glass ceramics, can also be used as a substrate. Most preferred are metals, such as titanium, and calcium phosphates, even though calcium phosphate is not an indispensable component of the substrate. The substrate may be porous or non-porous. The substrate may be biodegradable or bio-absorbable.

For example, MSCs of the invention that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating said support with a liquid suspension containing said cells. The impregnated supports obtained in this way can be implanted in a subject. Such impregnated supports can also be re-cultured by immersing them in a liquid culture medium, prior to being finally implanted.

The three-dimensional solid support needs to be biocompatible so as to enable it to be implanted in a subject. It can be of any suitable shape such as a cylinder, a sphere, a plate, or a part of arbitrary shape. Of the materials suitable for the biocompatible three-dimensional solid support, particular mention can be made of calcium carbonate, and in particular aragonite, specifically in the form of coral skeleton, porous ceramics based on alumina, on zirconia, on tricalcium phosphate, and/or hydroxyapatite, imitation coral skeleton obtained by hydrothermal exchange enabling calcium carbonate to be transformed into hydroxyapatite, or else apatite-wollastonite glass ceramics, bioactive glass ceramics such as Bioglass™ glasses.

The present invention is further illustrated by the following examples, which do not limit the scope of the invention in any way.

EXAMPLES

Materials and Methods

1. The Sampling Method: Muscular Microbiopsy

Microbiopsy procedures were performed on standing, awake horses. Microbiopsy specimens were obtained from triceps brachii muscles (long head, at the intersection of a vertical line extending from the tricipital crest and a line between the scapulo- and radio-humeral joints) of each horse (n=3).

Microbiopsy specimens were collected with a 14-gauge microbiopsy needle and a microbiopsy pistol. Briefly, the sampling site was shaved (one cm square) and aseptically prepared. Each sample (approximately 15 to 20 mg of tissue) was collected at a depth of 5 cm in the long head of the triceps brachii muscle, through a skin incision made with the tip of a scalpel blade nr 11. Closure of the skin incision was not necessary and the whole microbiopsy procedure was completed within 15 minutes. Immediately after collection, each sample was placed in 6 ml of culture medium composed of DMEM/F12 with 20% fetal bovine serum, 5 ml penicillin (1000 U/ml)-streptomycin (10000 µg/ml), 2.5 ml amphotericin B (250 µg/ml) and 5 ml HEPES [DF20]. Microbiopsy specimens were kept in growth medium at 4° C. until use.

2. Initiation of the Cell Cultures by Using Microbiopsy Specimens as Explants

Culture preparation was performed by use of sterile equipment, under a streamline flow hood. Microbiopsy specimens were washed twice in 5 ml of DF20 preheated to 37° C. Each microbiopsy specimen was carefully dissected (trying to keep as much as possible only muscular tissue) in 10 mM PBS solution (pH, 7.4) containing 137 mM NaCl and 2.7 mM KCl, then cut in small pieces (size of the tip of the scalpel blade). Then, each pieces was placed individually into the 16 central wells of 24-mutliwell dish, 100 µl of DF20 were added to each well, and culture dishes were incubated at 37° C. under controlled atmosphere (5% CO2 and 21% O2). The outer wells were filled with PBS (1 ml/well) to prevent drying out of well containing explants. Wells containing explants were monitored each day and fed by simple addition of new DF20 when necessary (keeping the growth factors within the wells).

When a halo of cells was visible around the tissue (about 10 days), the muscle pieces were individually transferred to another 24-multiwell dish (16 central wells for muscle pieces and the outer wells filled with PBS); the cells that had separated from the microbiopsy were grown to 80% confluence (about 20 days).

3. Trypsination of the Cells and Pluripotent Stem Cells Isolation: Discontinuous Percoll Density Gradient Centrifugation Nearly confluent cells obtained from explants were detached using tryspin-EDTA, centrifuged (200×g, 10 min, 37° C.) and the pellet was resuspended in 1 ml of HBSS. The cellular suspension was then placed on a discontinuous Percoll density gradient prepared as follows: Sodium Chloride solutions with 15%, 25% and 35% of Percoll were prepared. Then, 2 ml of each Percoll solution was added to a 15-ml culture tube to form the discontinuous Percoll density gradient above which 1 ml of the cellular suspension was placed. The cell fractions with different densities appeared at the interfaces between each Percoll fraction after centrifugation at 1250×g (25° C., 20 min). Each fraction (<15%, 15-25%, 25-35%) was individually collected, washed once with HBSS (1 ml/fraction) and centrifuged at 200×g, 10 min at 37° C. The supernatants were discarded and the pellets were resuspended in 1 ml of DF20/fraction. Each fraction was then cultured separately in T-25 cm$^2$ Flask until 80% confluence and finally, cells from each fraction were dissociated by use of trypsin-EDTA, in T-175-cm$^2$ Flask. Once reached 80% confluence (about 40 days), cells from <15%, 15-25% and 25-35% fractions could be frozen in liquid nitrogen or further passed for characterisation.

4. Characterization of the Cells

Cells from <15%, 15-25% and 25-35% fractions were characterized in number (cf. Point 4.1.), for their clonogenic capacities (cf. Point 4.2.), for their abilities to differentiate into adipocytes, chondrocytes and osteocytes when placed in adequate differentiation media (cf. Point 4.4.) and for their expression of CD29, CD105, CD44, CD90, CD45 and MHC II with flux cytometry (cf. Point 4.3.). All of these tests were performed before and after freezing the cells in liquid nitrogen. Cells from 15-25% and 25-35% fractions were also tested for their immunomodulatory capacities (cf. Point 5). Cells were also compared to Wharton's jelly and bone marrow MCSs for their expression miRNAs by RNA sequencing method (cf. Points 6 to 8).

4.1. Number of Cells

Once they were confluent, the number of cells contained in a 1-175 cm$^2$ Flask was evaluated for each cell fraction.

4.2. Clonogenic Capacity

The clonogenic capacities of the cells were evaluated with a "fibroblat-colony forming units" assay (CFU-F). Cells from each fraction, in primo-culture or after one passage, were seeded at low density (500000 cells/flask) and grown for 10 days. May-Grunwald Giemsa staining was used to visualise the colony forming units macroscopically and the total number of colonies/flask were counted.

4.3. Immunophenotyping

Harvested cells were analyzed by flow cytometry. Briefly, the cells ($10^5$) were washed with PBS and incubated with the following monoclonal antibodies:
CD29-FITC (Immunostep)
CD105-RPE (ABD Serotec)
CD44-APC (BD Pharmigen)
MCH II (ABD Serotec)
CD45-Alexa Fluor 488 (ABD Serotec)
CD90 (VMDR)

After washing with MACSQuant Running Buffer (Miltenyi Biotec), the cells were fixed with 4% formaldehyde solution. Data were acquired using MACSQuant Analyzer and evaluated using FCS Express 4 Flow Cytometry Software (De Novo Software, Los Angeles, Calif., USA).

4.4. Multi-Differentiation Potential of Cells

The differentiation potential of isolated cells was examined using cells harvested at P1 to P3. Adipogenic, osteogenic, and chondrogenic differentiations were performed according to the manufacturer's instructions in adapted media (NH media, Miltenyi Biotec).

Adipogenic Differentiation

For the adipogenic differentiation, 5000 cells/well were plated in a 24-well plate in NH AdipoDiff Medium (Miltenyi Biotec). After 7, 14, and 21 days, cells were colored using Oil Red O. Briefly, cells were washed with PBS and fixed with 8% formaldehyde before staining with Oil Red O solution (Sigma).

Chondrogenic Differentiation

To induce chondrogenesis, cells were transferred in the bottom of 15 mL conical tubes and differentiated into chondrocytes in pellet culture (250,000 cells/pellet) in 1 mL specific chondrocyte differentiation medium (NH ChondroDiff Medium; Miltenyi Biotec). Tubes were incubated for 21 days at 37° C. in a 5% $CO_2$ incubator, and the medium was replaced every week. Briefly, after 21 days, the micromasses were fixed with methanol and whole mount stained with alcian blue. Alcian blue was extracted with 6 mol/L guanidine hydrochloride and absorbance was read at 620 nm.

Osteogenic Differentiation

For the osteogenic differentiation, the cells were plated in DMEM in a 24-well plate at a density of 5,000 cells/well. After 24-48 h, the osteogenic medium (NH OsteoDiff Medium; Miltenyi Biotec) was added to the adherent cells. Every week, cells were fed with complete replacement of the medium. At days 7, 14, and 21, the calcium mineralization was assessed by coloration with Alizarin Red (Sigma), as described by Meloan et al. with slight modifications. Cells were washed in PBS and fixed in 70% ethanol at room temperature for 5 min followed by several washes in $H_2O$. Cells were stained in 40 mM Alizarin Red (Sigma) pH 4.2 for 15 min at room temperature, rinsed in $H_2O$, and then air dried. Red staining was examined by light microscopy.

The calcium accumulation was also measured (quantitative determination). To evaluate calcium deposition, the matrix was demineralized by addition of 200 µL of 0.6 N HCl and overnight incubation at 37° C. Solutions were then collected and centrifuged at 2,000 g for 5 min. Calcium concentration in the supernatant was determined by colorimetry (QuantiChrom Calcium Assays Kit; BioAssay Systems) as described by the manufacturer. Briefly, 5 mL samples were combined with 200 mL calcium reagent and incubated for 5 min at room temperature. The absorbance was measured immediately after incubation at 610 nm using a plate reader (Organon Teknika Cappel Products).

5. Evaluation of Immunomodulatory Capacities of Muscle-Derived MSCs

CD2 T-lymphocytes (TL) were purified from blood of horses collected on EDTA tubes by using magnetic beads. The CD2 TL population obtained showed a degree of purity of 99% (not shown). The CD2 TL were then fluorescent marked with carboxyfluorescein succinimidyl ester (CFSE), stimulated with phyto-hemagglutinin (PHA) and placed or not with the 15-25% or 25-35% fractions of the MSCs prepared by the method according to the present invention at different ratios MSCs/CD2 TL: 4/1, 2/1, 1/1, 1/2, 1/4 and 1/8. The inhibition of the CD2 TL proliferation (%) provoked by the MSCs was evaluated by the change in fluorescence observed and represents the immunomodulatory capacities of the MSCs.

6. Isolation of Mesenchymal Stem Cells from Wharton's Jelly.

Horse umbilical cord segments (5-10 cm) were sectioned longitudinally to expose the Wharton's jelly. Some incisions were made on the matrix with a sterile scalpel to expose a wider area of tissue to contact with the plastic surface. The cord sections were then transferred to a 10 cm2 Petri dish and plated for 5 days in Dulbecco's modified Eagle's medium with 1.0 g/L glucose, without L-glutamine (DMEM; Lonza) supplemented with 15% fetal bovine serum (Sigma), 2 mM LGlutamine (Lonza), and 0.5% antibiotic-antimycotic solution (Lonza). Cultures were maintained in a humidified atmosphere with 5% CO2 at 37° C. After 5 days, the cord segments were discarded and the medium was renewed. The cells were then expanded until they reached subconfluence (80-90%) with changing the medium every week. At subconfluence, the cells were harvested after detachment by 10 min incubation with TrypLE Select solution (Lonza). For passages, $5 \times 10^4$ cells were replated in 75 cm2 flask (Falcon) in the same culture conditions until subconfluence. Cells were passaged until P4.

7. Isolation of Bone Marrow-Derived Mesenchymal Stem Cells.

Briefly, mononucleated cells (MNC) (from horse bone marrow samples) were isolated by density gradient centrifugation (LinfoSep; Biomedics, Madrid, Spain) and washed in HBSS medium (Bio-Whittaker, Walkersville, Md.). We seeded $0.5 \times 10^6$ cells/ml in alpha-minimum essential medium (α-MEM; BioWhittaker) supplemented with 15% FBS (Biochrom, Berlin, Germany), 2 mM L-glutamine (GIBCO BRL, Grand Island, N.Y.), 0.5% antibiotic/antimycotic solution (GIBCO BRL). This is the complete α-MEM medium. MSCs, when selected by plastic adhesion, require the elimination of nonadherent cells by replacing the medium 48 hrs after cell seeding. When cultures reached 80% confluence, cells were detached with trypsin-EDTA solution (GIBCO BRL), and sub-cultured at $1 \times 10^4$ cells/ml.

8. Transcriptomic Analysis

Method

The RNA sequencing (RNA-seq) method was used. Total RNA was extracted from 20 million of MSCs prepared according to the method of the present invention (from the 15-25% fraction) from 2 different horses, 20 million of Wharton's jelly stem cells from 1 horse and 20 million of bone marrow derived stem cells from 1 horse using the RNAeasy mini kit (Qiagen). The cells were lysed in RLT buffer containing beta-mercaptoethanol, then the RNA was purified on column following manufacturer's recommendations.

RNA integrity has been verified on Bioanalyser 2100 with RNA 6000 Nano chips, RIN scores were >8 for all samples.

Illumina Truseq stranded mRNA Sample Preparation kit has been used to prepare libraries from 1 microgram of total RNA. Poly-A RNAs were purified with polyT-coated magnetic beads and chemically fragmented around 200 nucleotides. They are used as template for first strand synthesis in the presence of random hexamers and second strand synthesis after. Next, double strand cDNAs ends were adenylated at 3'OH extremities before the ligation to adaptors containing the indexes. Finally, the adapters-ligated library fragments were enriched by PCR following Illumina's protocol and purified with Ampure XP magnetic beads. Libraries were validated on Bioanalyser DNA 1000 chip and quantified by qPCR with the KAPA library quantification kit. Sequencing has been performed on Illumina NextSeq500 in paired-end 2×75 base protocol.

Data Analysis

Fastq files were trimmed for adaptor sequences. The reads were aligned with Tophat 2.0.9 to the horse genome (Equus caballus (Horse) EquCab2 from UCSC). Cufflinks 2.2.0 suite was used to generate FPKM values and CuffDiff was used to identify significantly differentially expressed genes.

Results

1. Sampling Method

The microbiopsy technique allowed for the acquisition of a sufficient amount of horse muscular tissue to easily initiate a culture. No contamination was observed, either during sampling or treatment in the laboratory, thus validating our working conditions. As each microbiopsy was cut into two pieces, it was possible to start two separate cultures with as little as 15-20 mg of tissue.

2. Culture by Explants

After three or four days in culture, the first cells started to appear around the sampled muscle. After about nine or ten days, the number of cells was sufficient for transplanting the explants and let the cells grown alone (so-called 1st cells). The transplanting explants allowed us to obtain a second pool of cells (so-called 2nd cells) that were also cultured till confluence. A third pool of cells can also be obtained. Furthermore, the 2nd cells started to appear around the piece of muscle faster than the 1st cells did.

3. Pluripotent Stem Cell Isolation

For each 3 horses and in each Percoll fraction (i.e. <15%, 15-25%, 25-35%), we succeeded to culture and to freeze an important amount of cells.

About 20 days after the initiation of the culture, the number of cells was sufficient to trypsinate and start the isolation process. Before this process, we obtained 1.020.000 and 1.340.000 of 1st cells for horse 2 and horse 3, respectively. The 2nd cells were 333.333 and 750.000 for respectively horse 2 and horse 3.

4. Characterization of the Cultured Cells 4.1. Number of Cells

|         |        | Primoculture | P1     | P2    |
|---------|--------|--------------|--------|-------|
| Horse 1 | <15%   | 1.42         | 6.816  |       |
|         | 15-25% | 4.56         | 16.41  |       |
|         | 25-35% | 4.44         | 76.368 |       |
| Horse 2 | <15%   | 3.42         | 184.7  | 5763  |
|         | 15-25% | 6.36         | 343.44 | 13325 |
|         | 25-35% | 3.78         | 249.5  | 7485  |
| Horse 3 | <15%   | 5.1          | 703.8  | 28152 |
|         | 15-25% | 3.24         | 395.3  | 5376  |
|         | 25-35% | 3.9          | 444.6  | 9425  |

Number of cells × $10^6$/ml

4.2. Clonogenic Capacity

|         |        | Primoculture | P1     |
|---------|--------|--------------|--------|
| Horse 1 | <15%   | 22           |        |
|         | 15-25% | 62           |        |
|         | 25-35% | 119          |        |
|         |        | CFU-F/5000 cells |    |
| Horse 2 | <15%   | 0.076        | 2.5    |
|         | 15-25% | 0.12         | 3.89   |
|         | 25-35% | 0.065        | 3.54   |
| Horse 3 | <15%   | 0.114        | 15.2   |
|         | 15-25% | 0.0615       | 10.277 |
|         | 25-35% | 0.7254       | 8.98   |
|         |        | CFU-F × $10^6$ |       |

The morphological aspect of the CFU's observed was different of the ones habitually observed with pluripotent stem cells isolated from bone marrow or Wharton's Jelly (FIG. 1).

In sections 4.1 and 4.2 above, P means "passage"; P1 is "passage1" and P2 is "passage 2". The term passage refers to "the transfer or subculture of cells from one culture vessel to another; usually, but not necessarily, involves the subdivision of a proliferating cell population, enabling the propagation of a cell line or cell strain.

The passage number is the number of times a culture has been subcultured.

5. Immunophenotyping

Figure 2:
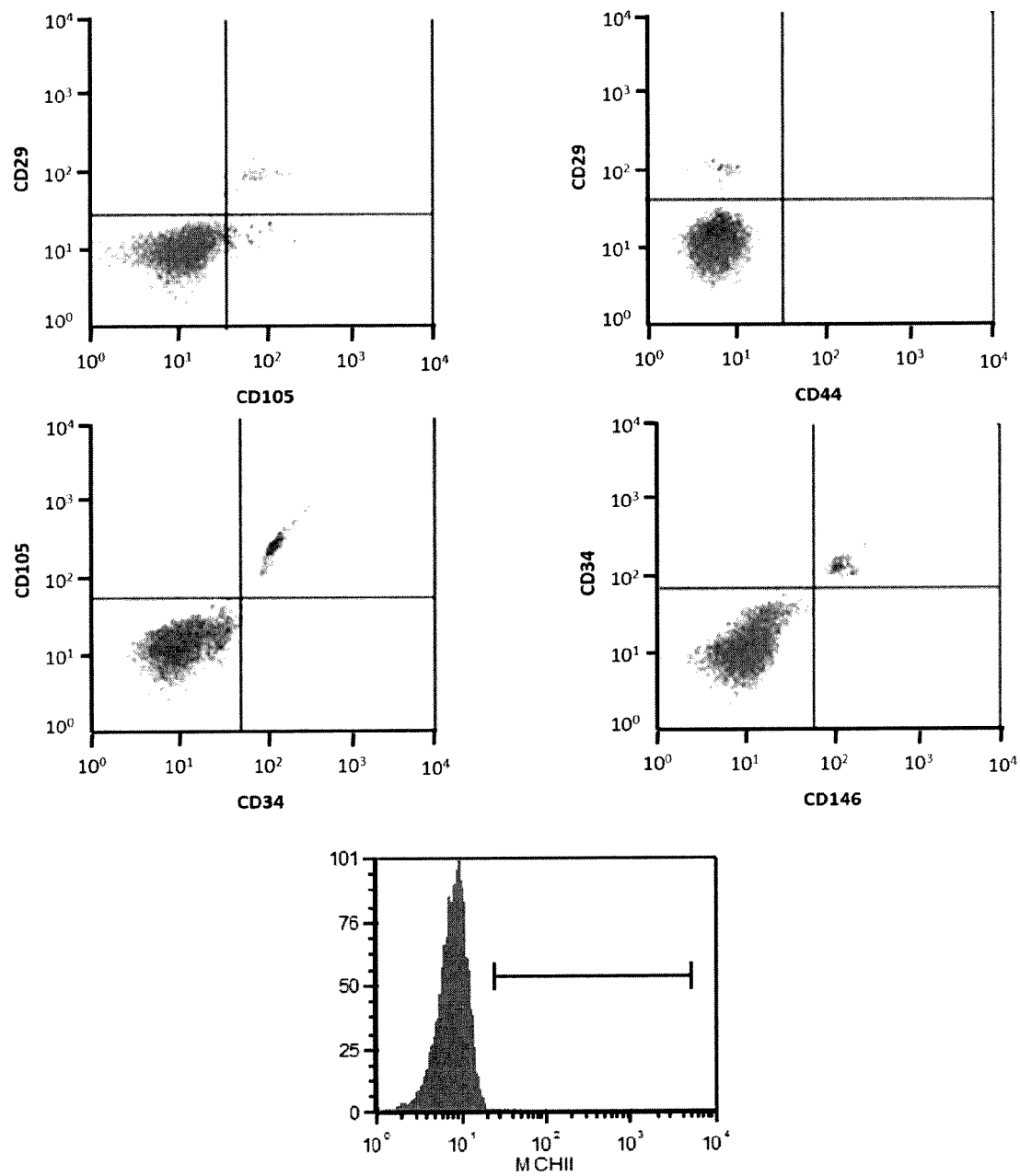
FIG. 2: Control FACS images showing the cross reactivity of the chosen antibodies on mononucleated cells from equine bone marrow.

The cells obtained were positive for CD44, CD90 and CD105 and negative for CD45, MHC II and CD29. The cross reactivity of all these antibodies with horse has been checked on mononucleated cells from equine bone marrows, except for CD29 (FIGS. 2 and 3).

Figure 3:
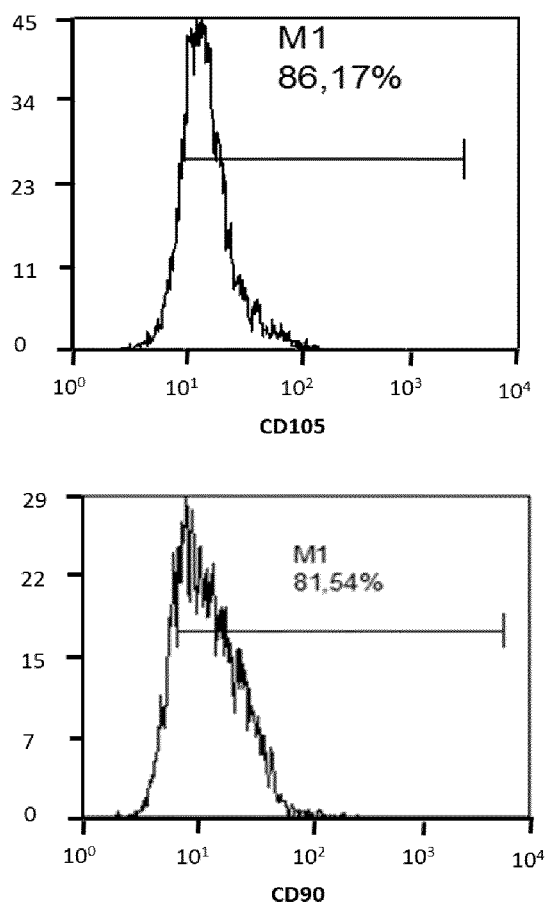
FIG. 3: Representative flux cytometry histograms of cells from 15-25% Percoll fraction (Horse 2). These cells are highly positive for CD105, CD90 and CD44 but negative for CD45.
Figure 3:
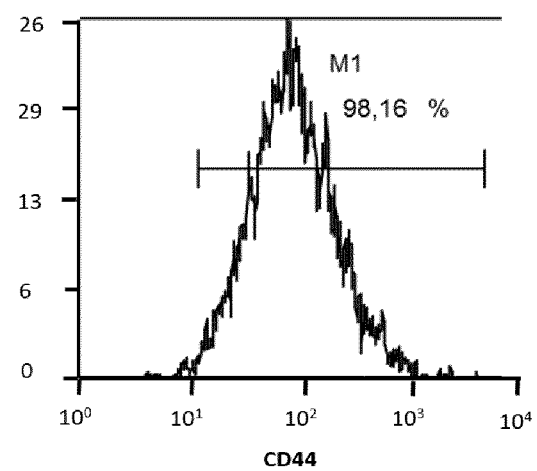
Figure 3:
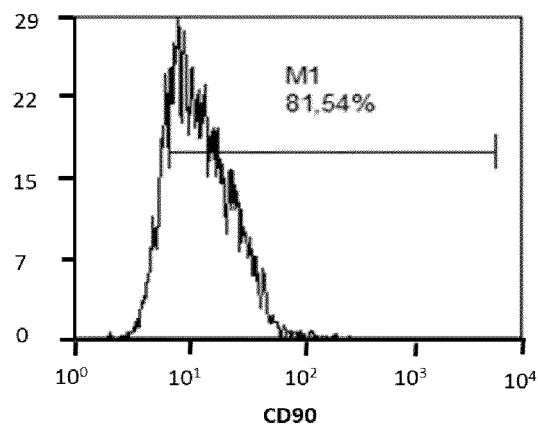
Figure 3:
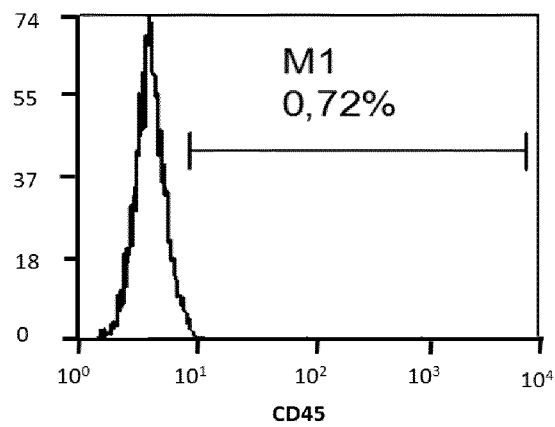

For each of the three Percoll fractions, 85-95% of the cells expressed CD105 and >90% of them expressed CD44 and CD90 (FIG. 3).

6. Multi-Differentiation Potential of Cells

Figure 4:
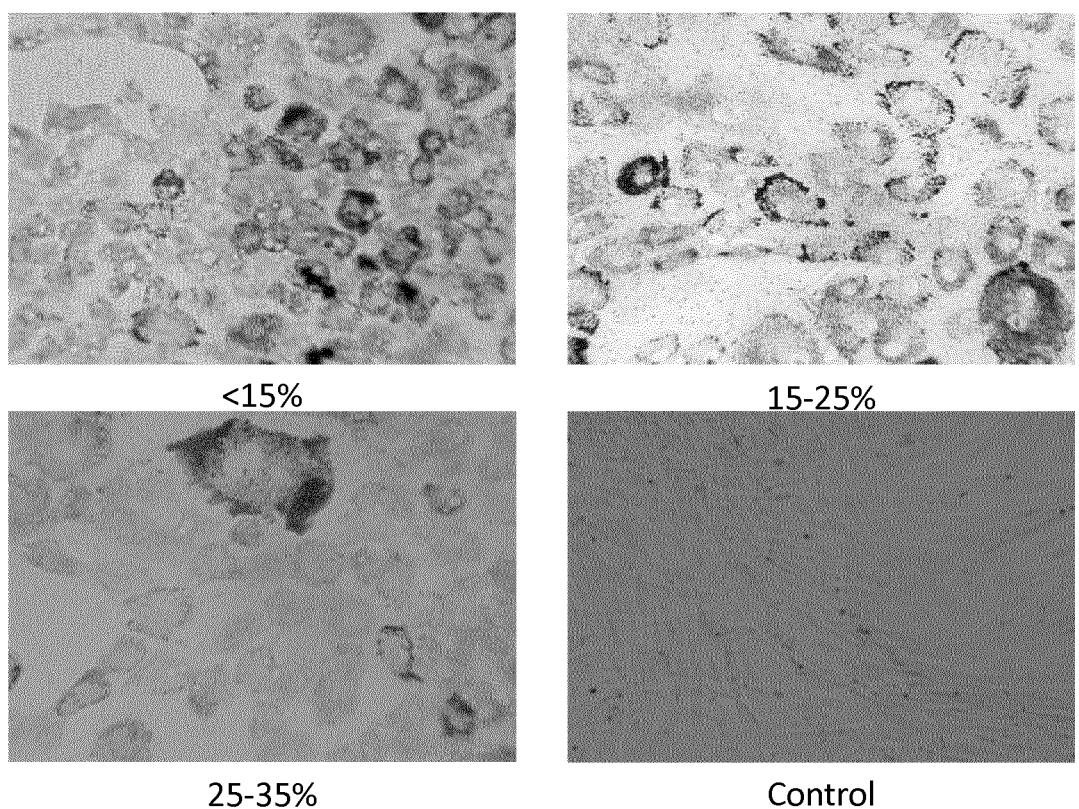
FIG. 4: Representative microscopic photographs of the adipocytic differentiation obtained for horse 2 after 7 days in differentiation medium (Oil Red 0 solution staining, 400× magnification). <15%, 15-25%, 25-35% represents the cells from the 3 Percoll fractions, Control represents the cells for which no differentiation was induced.
Figure 5:
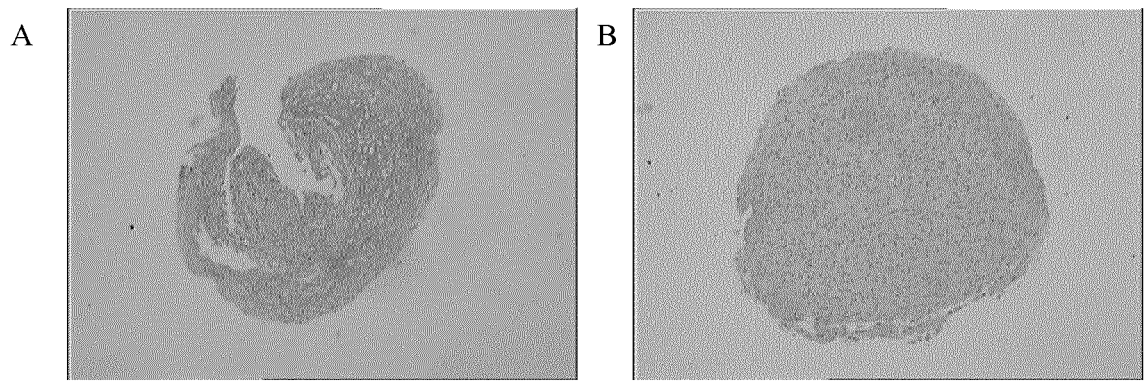
FIG. 5: Representative photographs of thin cuts staining with Alcian Blue, of the chondrosphere obtained after 3 weeks of culture in the chondrogenic differentiation medium (A) or of the control pellet (B; cells not cultured with chondrogenic differentiation medium).
Figure 6:
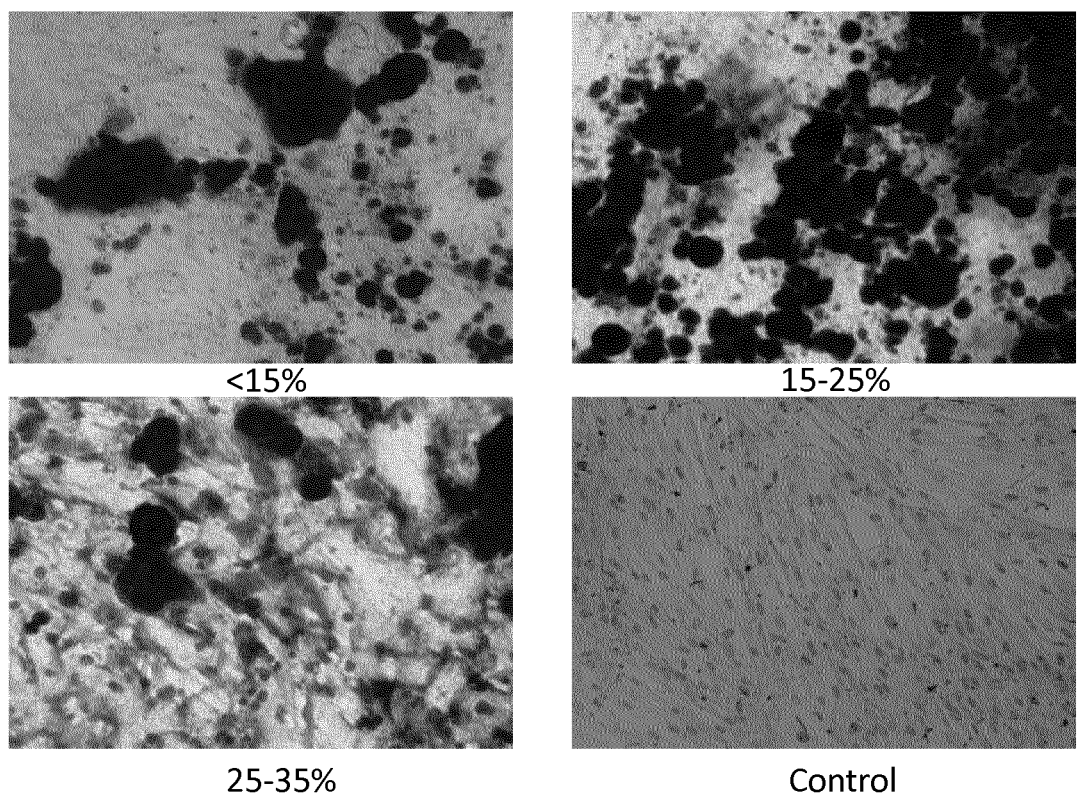
FIG. 6: Representative microscopic photographs of the osteogenic differentiation obtained for horse 2 after 7 days in differentiation medium (Alizarin Red solution staining, 400× magnification). <15%, 15-25%, 25-35% represented the cells from the 3 Percoll fractions, Control represented the cells for which no differentiation was induced.

The cells obtained from each of the three Percoll fractions were able to differentiate into adipocytes (FIG. 4), chondrocytes (FIG. 5) and osteocytes (FIG. 6) when cultured with the respective differentiation media.

7. Clinical Use of Cells

The horse MSCs obtained by the method according to the present invention are able to reduce lameness and to promote healing in horses affected by severe pathologies of the locomotor system such as desmitis, tendonitis and osteoarthritis. The MSCs can be administrated either directly in the lesions (tendon, ligament), or in the tendinous or articular synovials.

1/ Intratendinous Injection of MSCs

A race horse (mare, 9 years old, thoroughbred) developed a severe tendonitis of the superficial digital flexor tendon after a race. She received rest but no other treatment. Three months after the injury she showed a grade III left forelimb lameness, which was positive to the lower limb and the carpal flexions. The diagnostic imaging examination showed a postacute, healing superficial digital flexor tendon (SDFT) tendinopathy with strong vascularisation and core lesion. The method according to the present invention was used to obtain autologous MSCs from a muscular microbiopsy of the mare. A control was made six weeks later. There was no significant improvement of the lameness but the ultrasonographic examination showed a mild favorable evolution of the left anterior SDFT healing and softness of the core lesion. The mare received ultrasound-guided injection of $10^7$ autologous MSCs in the core lesion of the SDFT. She also received box resting with 20 minutes walking/day. Six weeks later, the mare showed a significant improvement of the left forelimb lameness. The ultrasonographic examination was significantly better, with an improved echogenicity (see table 1 below). The rehabilitation program is pursued.

A jumping horse (7 years old, Zangersheide, stallion) developed a right forelimb SDFT tendonitis. He responded well to rest and NSAIs (non-steroidal anti-inflammatory). He returned to previous level of performance 4 months later but developed another palmar swelling of the right forelimb after 3 weeks. He showed a grade III lameness associated to the swelling. The ultrasonographic examination showed a large hypoechoic, 5*1*0.7 cm, Doppler negative area with hyperechoic septa at the lateral aspect of the SDFT in the distal third of the 3rd metacarpal bone. He received corrective trimming, orthopedic shoeing and ultrasound-guided intralesional PrP injection. A rehabilitation program was suggested. A muscular microbiopsy was made for the preparation of MSCs according to the method of the present invention. The first control took place 8 weeks later. The swelling was totally resorbed and a 2 stages improvement of the lameness was noted. The ultrasonographic examination showed an improvement as well: the lesion was less hypoechoic reduced by 2 (2.5*0.5*0.7 cm) with a better fibrillar aspect. The horse received ultrasound-guided injection of $10^7$ autologous MSCs in the lesion of the SDFT. The rehabilitation program was pursued. At the second control (2 months later), the horse showed no lameness at all and the ultrasonography showed an ill-defined small hypoechoic area (see table 1 below). The horse received trimming, the orthopedic shoeing was maintained and the rehabilitation program was pursued. At the last control (2 months after the second control), there was no significant change in ultrasonographic images. The rehabilitation program was ended and the orthopedic shoeing maintained.

2/ Intratendinous and Intrasynovial Injection of MSCs

A leisure horse (gelding, 16 years old, half-blood) showed a grade III lameness of the left forelimb located below the fetlock. The imaging examination showed bilateral anterior tendinopathy of the medial lobe of the deep digital flexor tendon (DDFT) and light to mild degenerative joint disease of the left distal interphalangeal joint. Conventional intraarticular and orthopedic shoes were applied with no significant improvement after 6 weeks. The method according to the present invention was used to obtain autologous MSCs from a muscular microbiopsy of the gelding. Four weeks later, the horse received ultrasound-guided injection of $10^7$ autologous MSCs in the medial lobe of the left anterior deep digital flexor tendon and in the corresponding digital sheath. The horse showed local moderate swelling on the injection site for 2 days after the stem cells administration. Six weeks later a control was performed showing a mild improvement of the lameness and a light improvement of the ultrasonographic images. The rehabilitation program was started and at the second control, the horse was clearly better (see table 1 below). A progressive intensification of the physical activity was proposed.

3/ Intraligamentar and Intra-Articular Injection of MSCs

A leisure pony (gelding, 5 years) affected by a severe desmitis of the lateral collateral ligament of the right tarsocrural joint from 6 months and moderate signs of degenerative joint disease. Lameness III/V, swollen joint, painful flexion with limited range. Conventional treatments applied since the accident has not significantly improved lameness. The method according to the present invention was used to obtain autologous MSCs from a muscular microbiopsy of the pony. One month later, a dose of $10^7$ MSCs were injected in the ligament and $10^7$ MSCs in the synovial pouch of the tarso-crural joint. Six weeks later, a clinical improvement of the lameness was observed (grade I/V) with a clear decrease of the articular swelling and a normal flexion (see table 1 below). A program of rehabilitation was prescribed and the pony took over physical activity.

TABLE 1

Effect of the injection at specific sites of autologous horse MSCs prepared according to the method of the present invention ($10^7$/site of injection) on the lameness score [from 0: absence of lameness to V: impossibility for the horse to use the affected limb] of 4 horses with different osteo-articular diseases.

| | Diagnosis | Site of injection of autologous MSCs | Lameness score before injection (/V) | Lameness score after injection (/V) | Lameness score after 2$^{nd}$ control (/V) |
|---|---|---|---|---|---|
| Case 1 mare 9 y.o. thoroughbred | Tendonitis | Intratendineous | III | I | 0 |
| Case 2 gelding 16 y.o. half-blood | Tendinopathy and degenerative joint disease | Intratendineous and intrasynovial | III | 0 | 0 |
| Case 3 gelding 5 y.o. pony | Desmitis and degenerative joint disease | Intraligamentar and intraarticular | III | I | 0 |
| Case 4 stallion 7 y.o. Zangersheide | Tendonitis | Intratendinous | III | I | 0 |

8. Immunomodulatory Capacities of Cells

An inhibition of the proliferation (%) of the horse CD2 T Lymphocytes (TL) was observed. For the MSCs from the 15-25% fraction, the greater inhibition was observed with the ratio MSCs/CD2 TL of 1/8. For the cells from the 25-35% fraction, the optimal ratio of MSCs/CD2 TL was 1/2 (see table 2 below).

TABLE 2

Inhibition of the proliferation (%) of the CD2 TL of 2 horses when incubated with MSCs from the 15-25% or the 25-35% fractions at different ratios MSCs/CD2 TL (ie 4/1, 2/1, 1/1, 1/2, 1/4, 1/8).

| % inhibition of CD2 TL proliferation | 4/1 | 2/1 | 1/1 | 1/2 | 1/4 | 1/8 |
|---|---|---|---|---|---|---|
| Ratio MSCs 15-25%/CD2 TL | | | | | | |
| Horse C | 27 | 49 | 62 | 65 | 72 | 76 |
| Horse Cbis | 22 | 47 | 59 | 64 | 71 | 67 |
| Horse D | 0 | 17 | 27 | 28 | 38 | 40 |
| MEAN | 16.33 | 37.67 | 49.33 | 52.33 | 60.33 | 61.00 |
| SEM | 8.29 | 10.35 | 11.20 | 12.17 | 11.17 | 10.82 |
| Ratio MSCs 25-35%/CD2 TL | | | | | | |
| Horse C | 32 | 55 | 72 | 67 | 73 | 72 |
| Horse D | 0 | 8 | 33 | 46 | 41 | 37 |
| Horse Dbis | 19 | 54 | 68 | 72 | 71 | 72 |
| MEAN | 17.00 | 39.00 | 57.67 | 61.67 | 61.67 | 60.33 |
| SEM | 9.29 | 15.50 | 12.39 | 7.97 | 10.35 | 11.67 |

9. Transcriptomic Analysis—Differential Expression of 5 miRNAs Between Horse MSCs Prepared According to the Method of the Present Invention (Abbreviated as Muscle-Derived MSCs), Horse Wharton's Jelly MSCs and Horse Bone Marrow MSCs.

Figure 7:
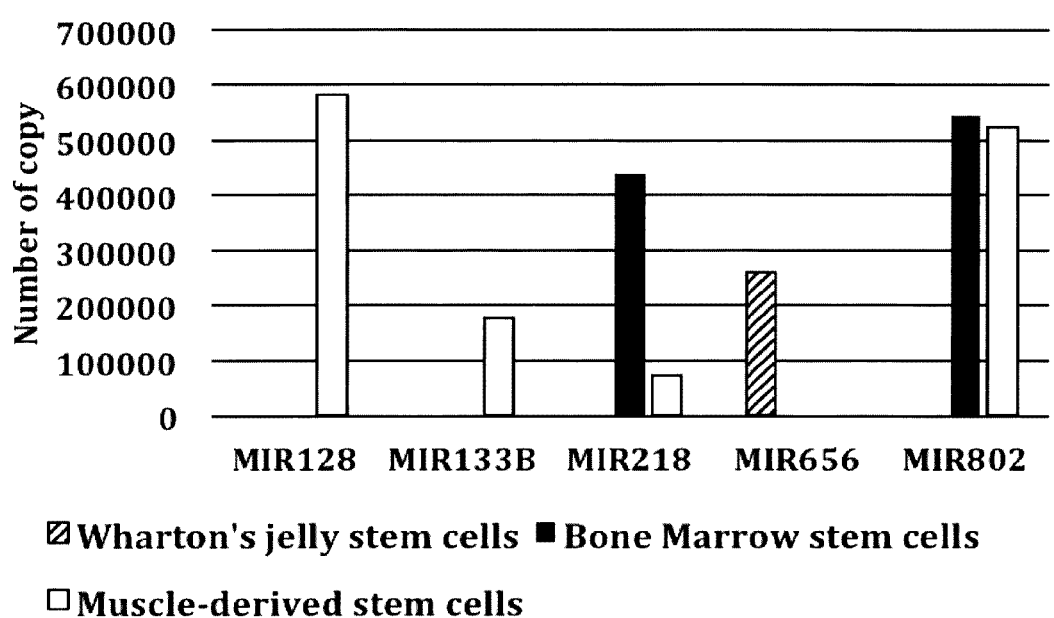
FIG. 7: Represents differential level of expression (number of copies detected) of 5 miRNAs in 3 sources of horse mesenchymal stem cells (MSCs), i.e. Wharton's jelly MSCs, bone marrow MSCs and muscle-derived MSCs according to the present invention.

We observed a significant differential expression for 56 genes between the 3 sources of stem cells. We choose to focus on microRNAs (miRNA). 5 miRNA, namely miR-128, miR-133B, miR-218, miR-656 and miR-802, showed a significant differential expression between the 3 sources of stem cells. Probably because of the technique used, the miRNAs observed are the precursors of the corresponding miRNA. From this experiment, it appears that miR-128 and miR-133B were significantly overexpressed in muscle-derived MSCs compared to Wharton's jelly MSCs and bone marrow MSCs. miR-218 and miR-802 were also expressed by muscle-derived MSCs but miR-218 was significantly higher expressed in bone marrow MSCs compared to Wharton's jelly MSCs and muscle-derived MSCs whereas miR-802 was significantly overexpressed in the bone marrow MSCs and muscle-derived MSCs compared to the Wharton's jelly MSCs. miR-656 was significantly overexpressed in the Wharton's jelly MSCs compared to the bone marrow MSCs and muscle-derived MSCs (FIG. 7).

ABBREVIATIONS

DF20: Growth culture medium composed of DMEM/F12 with 20% fetal bovine serum, 5 ml penicillin (1000 U/ml)-streptomycin (10000 µg/ml), 2.5 ml amphotericin B (250 µg/ml) and 5 ml HEPES.

HBSS: Hank's balanced salt solution

REFERENCES

Adams, M. K., Goodrich, L. R., Rao, S., Olea-Popelka, F., Phillips, N., Kisiday, J. D., McIlwraith, C. W. Equine bone marrow-derived mesenchymal stromal cells (BMDMSCs) from the ilium and sternum: Are there differences? Equine Veterinary Journal, 2012, 45, 372-375.

Ceusters J., Mouithys-Mickalad A., De La Rebière De Pouyade G., Franck T., Votion D., Deby-Dupont G., Serteyn D. Assessment of reactive oxygen species production in cultured equine skeletal myoblasts in response to conditions of anoxia followed by reoxygenation with or without exposure to peroxidases. American Journal of Veterinary Research, 2012, 73, 426-434.

Dominici, M., Le Blanc, K., Mueller, I., Slaper-Cortenbach, I., Marini, F., Krause, D., Deans, R., Keating, A., Prockop, D. J., Horwitz, E. Minimal criteria for defining multipotent mesenchymal stromal cells. The International Society for Cellular Therapy position statement. Cytotherapy, 2006, 8(4), 315-317.

Gutierrez-Nibeyro, S. D. Commercial cell-based therapies for musculoskeletal injuries in horses. Veterinary Clinics of North America: Equine Practice, 2011, 27, 363-371.

Iacono, E, Brunori, L, Pirrone, A, Pagliaro, P, Ricci, F, Tazzari, P L, Merlo, B. Isolation, characterization and differentiation of mesenchymal stem cells from amniotic fluid, umbilical cord blood and Wharton's jelly in the horse. Reproduction, 2012, 143, 455-468.

Meloan, S. N., Puchtler, H., Valentine, L. S. Alkaline and acid alizarin red S stains for alkali-soluble and alkali-insoluble calcium deposits. Archives of Pathology, 1972,93 (3),190-197.

Pittenger, M. F., Mackay, A. M., Beck, S. C., Jaiswal, R. K., Douglas, R., Mosca, J. D., Moorman, M. A., Simonetti, D. W., Craig, S., Marshak, D. R. Multilineage potential of adult human mesenchymal stem cells (MSCs). Science, 1999, 284 (5411), 143-147.

Radtke, C. L., Nino-Fong, R., Esparza Gonzalez, B. P., Stryhn, H., McDuffee, L. A. Characterization and osteogenic potential of equine muscle tissue- and periosteal tissue-derived mesenchymal stem cells (MSCs) in comparison with bone marrow- and adipose tissue-derived mesenchymal stem cells (MSCs). American Journal of Veterinary Research, 2013,74(5), 790-800.

Schnabel L. V., Fortier L. A., Wayne McIlwraith C., Nobert K. M. Therapeutic use of stem cells in horses: Which type, how, and when? The Veterinary Journal, 2013, 197(3), 570-577.

Usas, A., Mačiulaitis, J., Mačiulaitis, R., Jakubonienė, N., Milašius, A., Huard, J. Skeletal muscle-derived stem cells: implications for cell-mediated therapies. Medicina (Kaunas), 2011, 47(9), 469-479.

Votion D. M., Fraipont A., Goachet A. G., Robert C., Van Erck E., Amory H., Ceusters J., De La Rebiere De Pouyade G., Franck T., Mouithys-Mickalad A., Niesten A., Serteyn D. Alterations in mitochondrial respiratory function in response to endurance training and endurance racing. Equine Veterinary Journal, 2010, 42(suppl 38), 268-274.

What is claimed is:

1. A method for preparing mammalian mesenchymal stem cells (MSCs) comprising the steps of:
    a) collecting a microbiopsy from skeletal muscle tissue from said mammal,
    b) after collection, placing said microbiopsy in suitable culture medium,
    c) collecting cells emerging from said microbiopsy during culturing,
    d) growing the cells obtained in step c) to near confluency,
    e) dissociating the cells from step d),
    f) separating mesenchymal stem cells (MSCs) from the other cells by density gradient fractionation, thereby obtaining mesenchymal stem cells (MSCs).

2. The method according to claim 1, wherein said culture medium comprises DMEM/F12 with about 20% fetal bovine serum, about 5 ml penicillin (1000 U/ml)-streptomycin (10000 µg/ml), about 2.5 ml amphotericin B (250 µg/ml) and about 5 ml HEPES.

3. The method according to claim 1, wherein said mammal is selected from the group comprising: domestic and farm animals, zoo animals, sport animals, pet animals, companion animals, and experimental animals.

4. The method according to claim 1, additionally comprising the step of differentiating the cells into adipocytes, osteocytes, chondrocytes, myogenic cells, hematopoetic cells, endothelial cells, neural cells, cardiac cells, or hepatocytes by culturing the MSCs in an adequate adipogenic, osteogenic, chondrogenic, myogenic, hematopoetic, endothelial, neuronal, cardial, or hepatocytic differentiation medium respectively.

5. The method according to claim 3, wherein the animal is a mouse, rat, hamster, rabbit, dog, cat, guinea pig, cow, sheep, horse, pig, or primate.

6. The method according to claim 5, wherein the animal is a primate, and wherein the primate is a monkey or an ape.

7. The method according to claim 1, wherein the method is performed in the absence of enzyme degradation.

8. The method according to claim 1, wherein the mesenchymal stem cells express CD105, CD44, and CD90.

9. The method according to claim 8, wherein the mesenchymal stem cells do not express CHD45, MHCII, and CD29.

10. The method according to claim 8, wherein the mesenchymal stem cells express at least one of miR-128 and miR-133B and do not express miR-656.

* * * * *